United States Patent
Park

(10) Patent No.: US 12,290,446 B1
(45) Date of Patent: May 6, 2025

(54) CUSTOMIZED KNEE PROSTHESIS AND ARTHRITIC KNEE RESTORATION PROCESS

(71) Applicant: Lento Medical Inc., Houston, TX (US)

(72) Inventor: Ilwhan Park, Katy, TX (US)

(73) Assignee: Lento Medical Inc., Houston, TX (US)

( * ) Notice: Subject to any disclaimer, the term of this patent is extended or adjusted under 35 U.S.C. 154(b) by 398 days.

(21) Appl. No.: 17/989,665

(22) Filed: Nov. 17, 2022

Related U.S. Application Data

(60) Provisional application No. 63/280,350, filed on Nov. 17, 2021.

(51) Int. Cl.
*A61F 2/30* (2006.01)
*A61F 2/38* (2006.01)
(Continued)

(52) U.S. Cl.
CPC ........ *A61F 2/30942* (2013.01); *A61F 2/3859* (2013.01); *A61F 2/3877* (2013.01); *A61F 2/389* (2013.01); *G06T 7/13* (2017.01); *G06T 7/174* (2017.01); *G06T 7/60* (2013.01); *G06T 7/73* (2017.01); *G16H 30/40* (2018.01); *A61F 2002/30952* (2013.01); *A61F 2002/4668* (2013.01); *G06T 2207/10081* (2013.01); *G06T 2207/10088* (2013.01)

(58) Field of Classification Search
CPC .. A61F 2/30942; A61F 2/3859; A61F 2/3877; A61F 2/389; A61F 2002/30952; A61F 2002/4668; G06T 7/13; G06T 7/174; G06T 7/60; G06T 7/73; G06T 2207/10081; G06T 2207/10088; G16H 30/40

See application file for complete search history.

(56) References Cited

U.S. PATENT DOCUMENTS 11,357,634 B1   6/2022   Hajizadeh
11,382,757 B1   7/2022   Hajizadeh et al.
(Continued)

OTHER PUBLICATIONS

Article: Xavier Gasparutto et al., "Kinematics of the Normal Knee during Dynamic Activities: A Synthesis of Data from Intracortical Pins and Biplane Imaging", Applied Bionics and Biomechanics, vol. 2017, Article ID 1908618, 9 pages.

*Primary Examiner* — Christopher Wait
(74) *Attorney, Agent, or Firm* — Mark Protsik; Thomas Schneck

(57) ABSTRACT

A computer-aided method, using a pre-operative planning software tool and patient-specific images, establishes implant parameters that customize selection of a total knee replacement prosthesis. The computer system determines from coronal, axial and sagittal image slices of a knee joint a neutral boundary axis, a set of epicondylar and trochlear features that define an elliptical cam, and a medial-lateral tibial slope, then defines from overlapping condylar and trochlear circles an ellipse with eccentricity 0.25 and focal points coincident with the circles. A knee prosthesis has a femoral component as an elliptical cam with dimensions defined by the ellipse, and has tibial and patellar components interacting with the femoral component as cam followers under knee flexion. A prosthesis is selected from a set with differing coronal asymmetry angle α to closely match the patient α as estimated from the images.

9 Claims, 20 Drawing Sheets

(51) Int. Cl.
*A61F 2/46* (2006.01)
*G06T 7/13* (2017.01)
*G06T 7/174* (2017.01)
*G06T 7/60* (2017.01)
*G06T 7/73* (2017.01)
*G16H 30/40* (2018.01)

(56) References Cited

U.S. PATENT DOCUMENTS 11,439,467 B1 9/2022 Park
2021/0192759 A1* 6/2021 Lang .................... A61B 90/98

* cited by examiner

FIG. 4A      FIG. 4B

CUSTOMIZED KNEE PROSTHESIS AND ARTHRITIC KNEE RESTORATION PROCESS

CROSS-REFERENCE TO RELATED APPLICATION

This application claims priority under 35 U.S.C. 119 (e) from U.S. provisional application 63/280,350 filed on Nov. 17, 2021.

TECHNICAL FIELD

The invention relates to design customization of a knee implant based on patient-specific parameters and to methods for restoration of arthritis knees using such customized implants.

BACKGROUND ART

Several custom knee implants have been put on the Market (e.g., by Comformis, Inc). These implants are focused on medial-lateral (ML) and anterior-posterior (AP) lengths, while ignoring asymmetric characteristics of femoral condyles and tibial plateau. Accordingly, many so-called custom design implants are symmetric implants, even though the anatomical knee condyles are naturally asymmetric. Furthermore, the tibial plateau of these implants is symmetric too. A usual reason for ignoring the anatomical asymmetries in implant designs is the difficulty in constructing a suitable 3D model of a patient's knee due to arthritic knee damage. As a result of arthritis, some information regarding certain femoral and tibial landmarks or features is missing from MRI or CT images. Because of a lack of information to determine pre-arthritic joint parameters, designers have been forced to rely only on existing joint surface contours and symmetric implants have been used.

SUMMARY DISCLOSURE

A process for customizing a knee prosthesis is provided that is based upon using current scan images of a patient's knee to determine elliptical cam parameters for an asymmetric implant that will be functionally equivalent to that knee's restored pre-arthritic condition. The process identifies a set of landmarks on MRI and CT axial/coronal/sagittal images and, using two circles as a base, generates an implant profile that includes asymmetric femoral and tibial characteristics, and not solely medial-lateral and anterior-posterior dimensions of joint surface profiles, to preserve the functionality of normal knee motion. Based on the identified points, graphs and equations, the restoration procedure of the distal femur, proximal tibia and patella leads to a programmable method to generate customized 3D knee implants.

Two conditions needed to apply this novel technique are:
1) Medial and Lateral Epicondyles are preserved in arthritis knee. 99% of arthritis knees show the epicondyle landmarks are not damaged by osteophytes and fractures.
2) At least, one of condyles should be preserved with no or minor damages (99%). If both condyles are significantly damaged, the restoration of this kind of arthritic knee cannot be restored.

If those conditions are met, then based on key landmarks or features related to gravity, wear mechanisms and Ptolemy circles geometric analysis, a different way of looking at the knee as an elliptical cam with 3D rotation during flexion and extension leads to a highly reliable restoration of the damaged knee due to arthritis substantially to its pre-arthritic condition. Around 20 to 25 anatomical landmark points need to be identified from the MRI or CT images. It leads to the generation of axial, coronal, sagittal implant profiles of the knee. From this point, 3D model generation is trivial. Based on gravity wear mechanisms, graphs and equations, information that would otherwise be missing due to arthritis is restored. The implant design then starts with two circles obtained from the landmark points and generated 3D model. Using an elliptical cam model of the knee, the two circles establish parameters for how both tibia and trochlear groove will rotate in an asymmetric implant. Based on these techniques, the outcome will be a prosthesis that when implanted allows flexion to equal or exceed 140°, and more often obtain 155° flexion, and in a few cases still greater flexion up to about 165°. This is a substantial improvement over the typical 90° range of flexion.

BRIEF DESCRIPTION OF THE DRAWINGS

FIG. 2A is a knee joint image in coronal view overlaid with a line Me-Nl extending from the medial epicondyle Me perpendicular to the NBA axis.

In FIG. 3A, approximation of the surface characteristics of the medial femoral condyle is based on a point at the distal medial femoral condyle point (P1), a point at the posterior medial femoral condyle (P2) and a third point representing the deepest point of flexion (P3). A circle is aligned to these three points which has a center point Fc. In FIG. 3B, approximation of the surface characteristics of the trochlear groove based on three points Q1, Q2, and Q3. Another circle is aligned to these three points. In FIG. 3C, the two geometric circles define center points Fc and Ft and an equivalent radius (R). The two circles have center points that are separated by radius R. In FIG. 3D, the centers of the circles align with the epicondyles in the axial plane (i.e., Fc aligns with the lateral epicondyle and Ft aligns with the medial epicondyle).

FIGS. 4A and 4B are knee joint sagittal cut planes for representing an elliptical mode of the distal femur. In FIG. 4A, an ellipse with centroids Fc and Ft is shown in relationship to the medial distal femoral condyle point Pm1. The ellipse has a center point, O, and is coincident with the three points along the medial femoral condyle PM1 (distal), PM2 (posterior), and PM3 (end). In FIG. 4B, an ellipse is represented on the lateral distal femoral condyle. The portion of the lateral femoral condyle contour that is highlighted by the dashed line represents the asymmetric surface contour. The ellipse is coincident with the medial-lateral condyle converging point PC and with three points along the lateral femoral condyle PL1 (distal), PL2 (posterior), and PL3 (end) and is not coincident from points PM1 to PC. This asymmetric portion of the lateral femoral condyle is termed the sagittal asymmetric angle (angle µ).

In FIGS. 7A-7C, V/V angle is 0.1° valgus, α=0.5°, and ϕ=0.3°. In FIGS. 7D-7F, V/V angle is 1.7° valgus, α=3.7°, and ϕ=3.9°. In FIGS. 7G-7I, V/V angle is 2.1° varus, α=4.2°, and ϕ=5.3°. FIGS. 7C, 7F and 7I, graph the lateral and medial tibial plateau cartilage surface for the three cases.

FIGS. 8D-8E show the position of the sectional cut plane A-B for FIG. 8C, which shows that the surface profile of A-B cross section is very close to that of distal condyles of femur.

DETAILED DESCRIPTION

Applicant incorporates by reference the material contained in U.S. Pat. No. 11,357,634 to Hajizadeh issued Jun. 14, 2022, in U.S. Pat. No. 11,382,757 to Hajizadeh and Park issued on Jul. 12, 2022, and the material contained in U.S. Pat. No. 11,439,467 to Park issued on Sep. 13, 2022. The inventor for the present application, Ilwhan Park, is also a co-inventor or sole inventor of two of these patents and their content is herein incorporated as background for understanding the present invention.

Model Development

To generate an asymmetric implant that is functionally identical to a specific patient's knee, we need to model the existing joint profile of that knee based on MRI or CT images in axial, coronal, and sagittal plane views. A set of twenty to twenty-five physical landmarks identified from those images allows femoral axes to be defined, a geometric model of the femoral condyles and trochlear groove as an elliptical cam to be developed using two overlapping epicondyle and trochlear circles from the images as elliptical focal points, asymmetric parameters α, β, and µ to be calculated, and the medial-lateral tibial slope difference ϕ to be calculated. These are used to select the appropriate asymmetric implant for each patient.

Defining the Femoral Axes

Figure 1A:
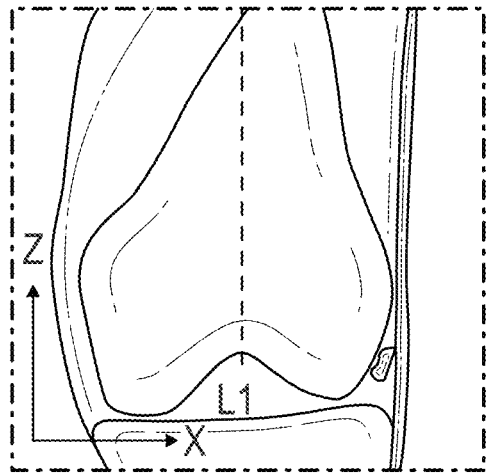
FIG. 1A is knee joint image overlaid with the neutral boundary alignment (NBA) axis L1 in a coronal (x-z) plane.
Figure 1B:
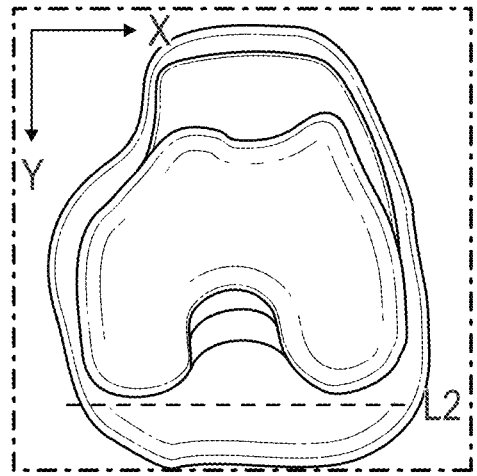
FIG. 1B is a knee joint image overlaid with the posterior condyle line (PCL) L2 in an axial (x-y) plane perpendicular to the NBA of FIG. 1A.
Figure 1C:
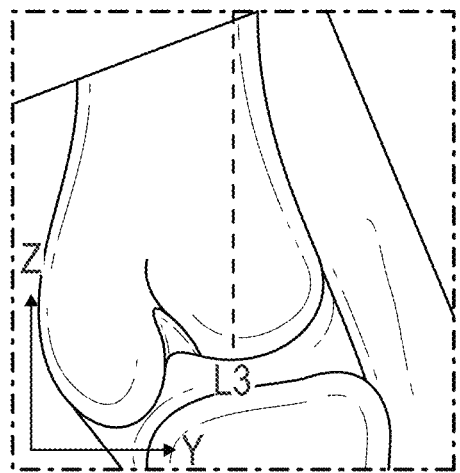
FIG. 1C is a knee joint image overlaid with the femoral mechanical axis (MA) L3 in a sagittal (y-z) plane defined from the center of the femoral head and center of the knee.

The femoral articular surface model relies on three axes in the coronal, sagittal and axial planes of MRI or CT images of a patient's leg. The coronal axis is defined based on the Neutral Boundary Alignment (NBA) axis L1 (FIG. 1A). This axis is akin to the mechanical axis (MA) but varies by the joint line orientation. In NBA, the joint line is like the description of the anatomical axis (AA), which is parallel to the ground; however, is defined as such during the single leg stance phase of the gait cycle. The axial axis is defined based on the posterior condylar line (PCL) L2 (FIG. 1B). It is noted that the orientation of the axial femur is perpendicular to the NBA (as opposed to the MA), when defining the axial axis here. The sagittal axis is defined as the femoral mechanical axis L3 (i.e., center of the femoral head to the center of the knee in the sagittal plane) in the sagittal view (FIG. 1C).

Figure 2C:
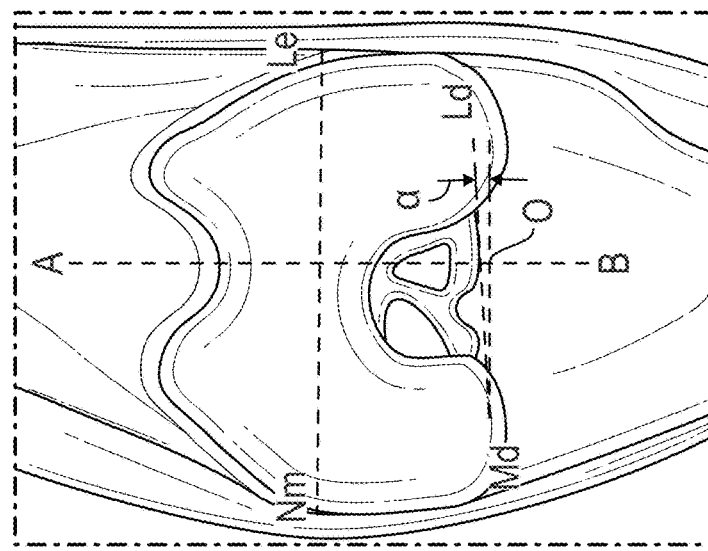
FIG. 2C is a knee joint image in coronal view for defining a coronal asymmetry angle (CAA) (angle α) between the NBA axis of FIG. 1A (line Nm-Le and parallel line Md-O) and the joint line Md-Ld defined by the distal femoral condyle points Md and Ld.
Figure 2B:
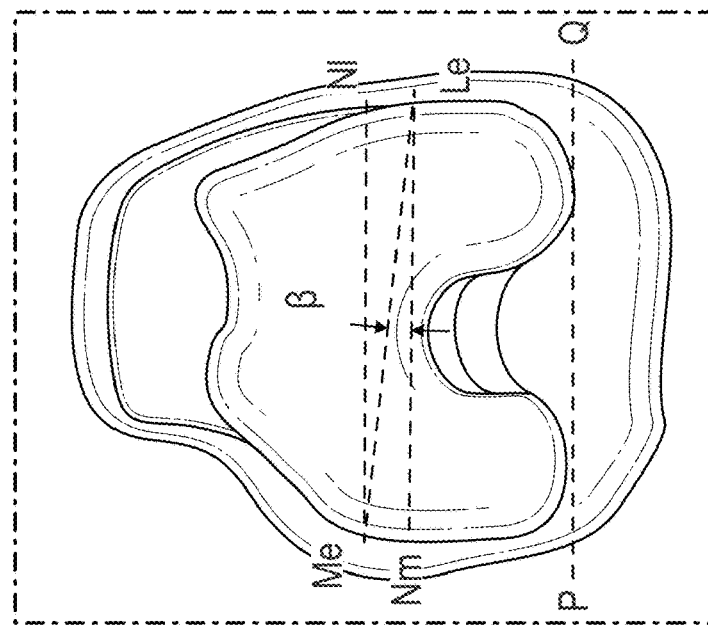
FIG. 2B is a knee joint image in axial view for defining an axial asymmetry angle (AAA) (angle β) between the PCL of FIG. 1B (line P-Q and parallel lines Me-Le and Le-Nm) and a trans-epicondylar axis Me-Le.
Figure 2B:
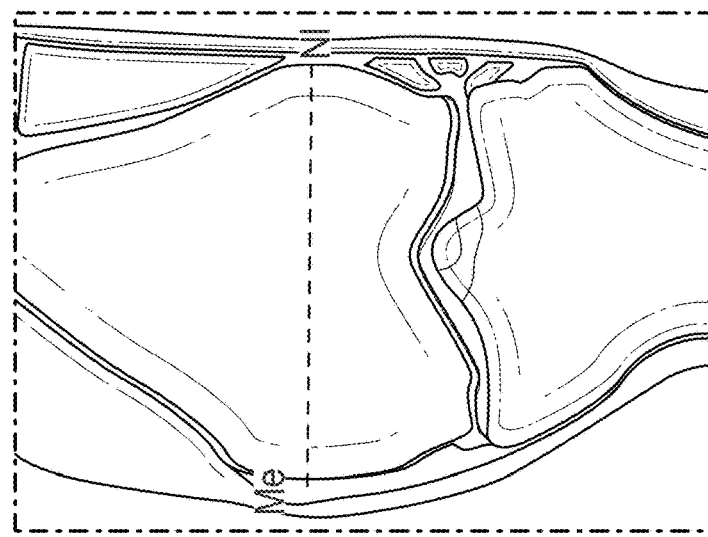

Using the NBA in the coronal plane and the PCL in the axial plane, two angles of asymmetry are defined. The first angle β is defined with respect to the lateral and medial epicondyles. In FIGS. 2A-2C, the lateral and medial epicondyles are identified as Le and Me in the coronal view (FIGS. 2A and 2C) and axial view (FIG. 2B). Note that the medial and lateral epicondyles Le and Me lie approximately on the same axial plane with respect to the NBA. This first angle of asymmetry specifies the orientation of the epicondyles in relation to the PCL. It can be found by creating lines, Me-Nl and Le-Nm, which are each perpendicular to NBA and parallel to the PCL, and a line connecting the two epicondyles in the axial plane Me-Le. The angle formed between these lines creates the axial asymmetric angle (AAA), which we notate angle β (FIG. 2B). Next, we define a second angle α of asymmetry, which again relies on the NBA. This angle is formed between the joint line created by the distal points of the femoral distal condyles (Md and Ld, FIG. 2C) and a line perpendicular to the NBA. This second angle represents the coronal asymmetric angle (CAA) and is notated as angle α (FIG. 2C).

Figure 2D:
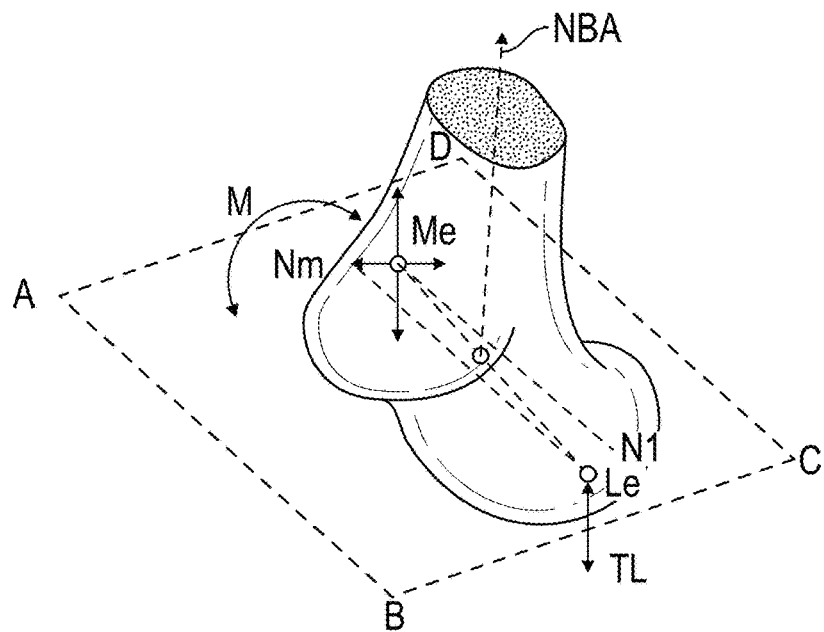
FIG. 2D is a perspective view representing the relationship of the medial and lateral epicondyles with the NBA axis.

The relationship between these angles and landmarks is visualized in a 3-D diagram in FIG. 2D. We postulate that the axial asymmetric angle β is important in providing varus/valgus and rotational stability of knee joint in full extension. Furthermore, when the knee initiates flexion, the MCL and LCL tension (TM and TL) induces a moment which causes the knee to initially rotate with respect to NBA. The orientation of the epicondyles, which is captured with angle β, not only assists in the initial knee rotation, but also determines the amount of moment involved. The greater the value of angle β, the greater the moment can be induced for knee rotation. It is noted that MCL is a strong broad band found at the medial epicondyle on the inner aspect of the knee joint which is the largest structure situated on the medial side. Therefore, it is deduced that the knee system is delicate passive mechanism for controlling tensions of MCL and LCL in harmony with knee surface physical characteristics.

Figure 2E:
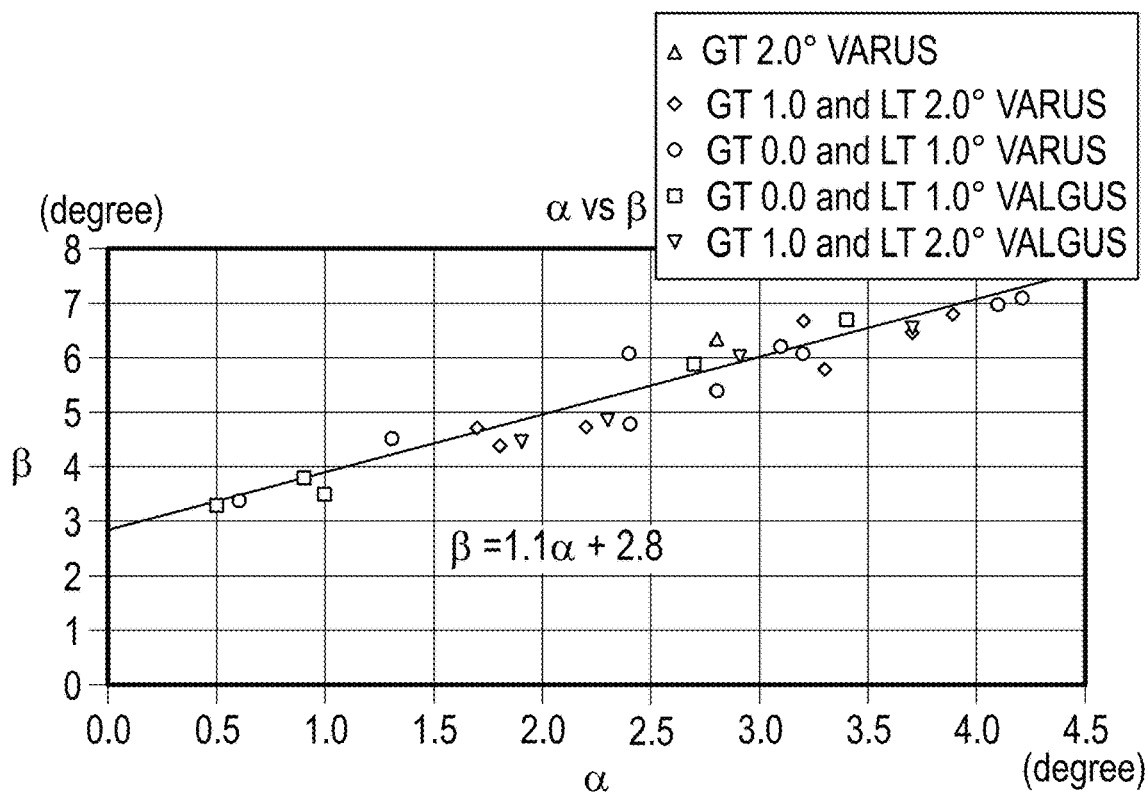
FIG. 2E is a graph of the best bit linear relation between the CAA (angle α) and the AAA (angle β) for various varus and valgus knee joints. When angle α goes to zero (i.e., NBA is perpendicular to joint line), then the angle β becomes close to 3°.

The two angles, α and β, vary between individuals and show no correlation with varus or valgus knee alignment. It is found that the average α is 2.5°±1.1°, and the average β is 5.5°±1.2°. However, we do find that there is a functional linear relationship between angles α and β (FIG. 2E). As angle α increases, so does angle β. From this observation, it is deduced that the higher the CAA becomes, the higher the moment is required in AAA to execute the knee rotation as knee flexes from full extension. Notably, as angle α goes to zero, it is seen that β approaches to 2.8° or close to 3°. This 3° relation between the PCL and the TEA occurs when the medial and lateral condyles are nearly symmetric and is consistent with the 3° relationship between PCL and TEA when performing TKA with respect to the MA.

With a precisely calculated from the patient's MRI or CT images, as described, the choice of an appropriate prosthesis can be made. If α≤2.5°, a symmetric implant can be used. But if α>2.5°, as will often be the case, an asymmetric prosthesis is needed. One with a 2.5° asymmetry is usually the most appropriate, except for the more extreme cases where α>3° where a prosthesis with 3° asymmetry may be selected. For economy, prostheses will generally be selected from a premade set that offers specific degrees of coronal asymmetry α (e.g., in 0.5° increments), rather than custom making of each prosthesis to an exact patient match.

Geometrical Model Development

Figure 3A:
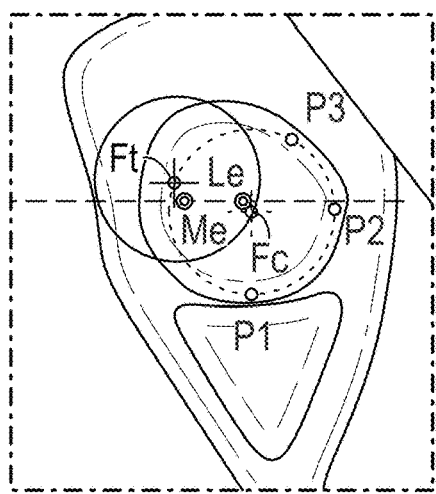
FIGS. 3A-3D are knee joint sagittal cut planes for representing the trochlear groove and medial and lateral epicondyles.
Figure 3B:
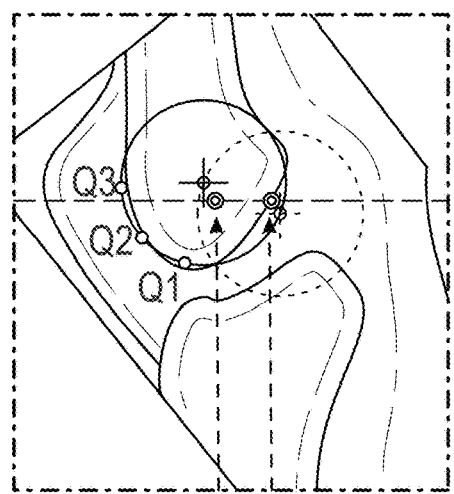
Figure 3C:
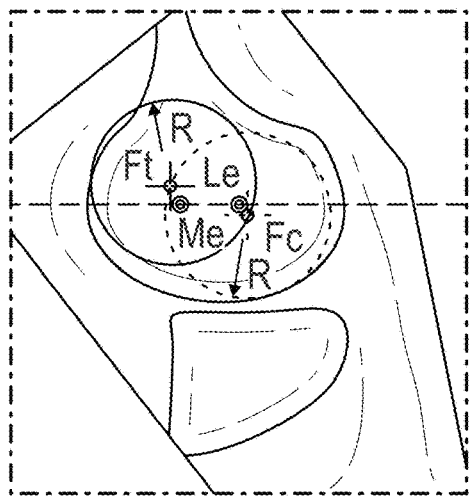
Figure 3D:
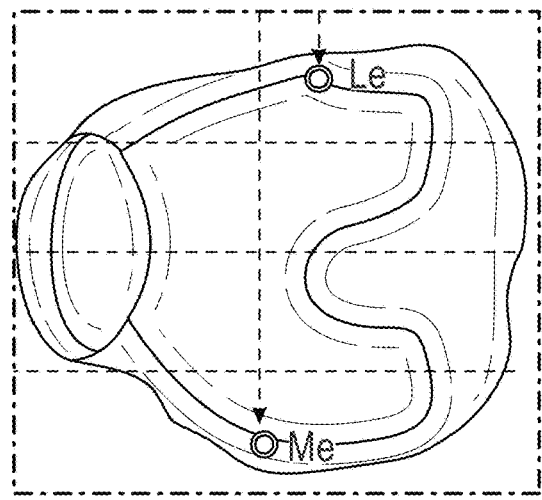
Figure 3E:
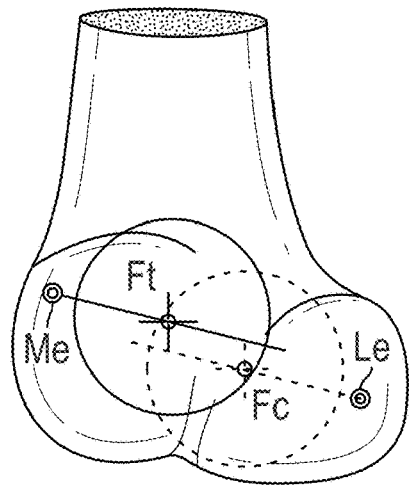
FIG. 3E is a perspective view of the distal femur and representing the two defined geometric circles determined from FIGS. 3A-3D.

We can now proceed to generate a geometrical model of the contours of the femoral distal condyles and the trochlear groove when the femur is aligned according to the NBA and the PCL. Three sagittal cuts of the distal femur are used (FIG. 3A-3D). These are the sagittal cross-sections of the medial and lateral condyles (FIGS. 3A and 3C) when the most posterior point of each condyle is in view, and the trochlear groove at the deepest aspect (FIG. 3B). In the corresponding view, the medial condyle is modeled by a circle which aligns to three points (FIG. 3A): 1) the most distal point of the condyle (P1); 2) the most posterior point of the condyle (P2); 3) the end of the medial condyle, which represents the point of deepest flexion (P3). The circle approximated by these three points, subsequently defines a center point (Fc) and a radius of curvature R (FIGS. 3A and 3C). Next, it is possible to find another circle about the trochlear groove that has the same radius of curvature (R). This circle is similarly approximated by three points on the trochlea (FIG. 3B): 1) a distal trochlear groove point (Q1); 2) a mid-trochlear groove point (Q2); 3) and lastly, an anterior trochlear groove point (Q3). The circle created by these points defines another center point (Ft) with an equivalent radius of curvature (R) as that formed by the medial condyle (FIG. 3C). FIG. 3E shows the relation in the 3-D femur model. It is found that the size of the circle obtained on the trochlear is geometrically compatible to that of the medial condyle. Herein, the sizes, i.e., radius, of the two circles are assumed identical in the modeling process.

Figure 4C:
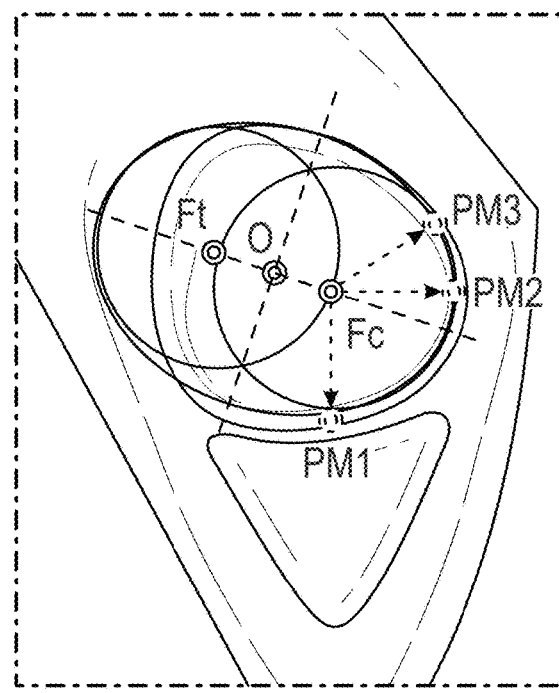
FIG. 4C is a perspective view of the distal femur and representing the elliptical model determined from FIGS. 4A and 4B.
Figure 4C:
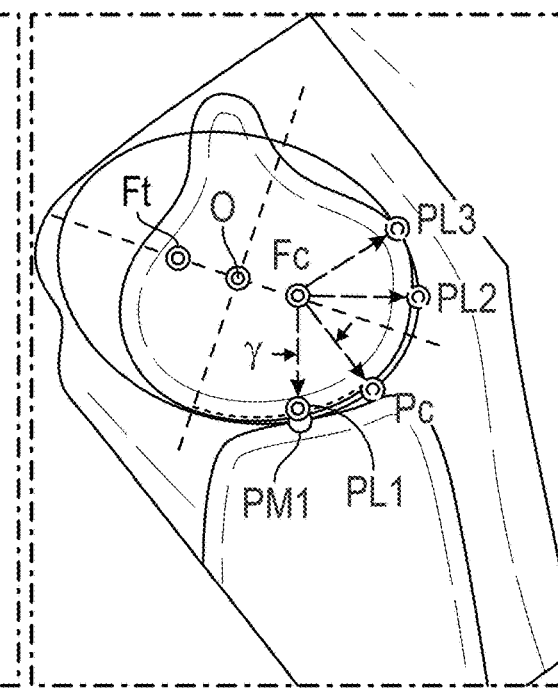
Figure 4C:
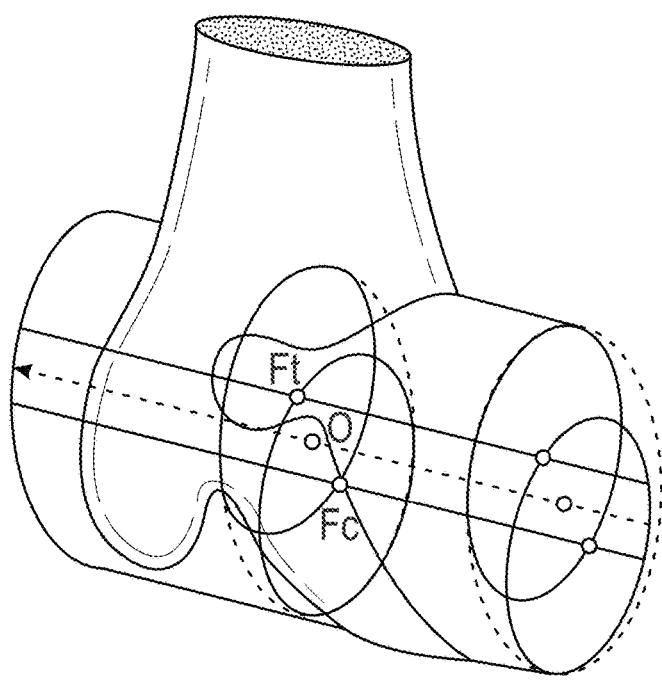

The two center points defined by these circles, Fc and Ft, are then used to define focal points of an ellipse with the center point (Q) (FIG. 4A). The eccentricity of this ellipse tends to be around 0.25. Each implant will use the same 0.25 eccentricity in its design. Additionally, the two points Fc and Ft are situated in proximity to the lateral epicondyle and medial epicondyles, respectively. The center point (Q) of the elliptical model could be considered as the dynamic center of the distal femur regarding rotation and flexion When the ellipse is overlayed on the lateral condyle (FIG. 4B), the ellipse closely approximates the posterior portion of the condyle but does not match the distal aspect of the condyle. As can be seen from FIG. 4B, the portion of the lateral condyle that does not match begins at point Pc and extends to the distal aspect of the condyle to PL1. On the other hand, both medial and lateral condyles approximate the elliptical model posterior to point Pc (i.e., PL2≈PM2, and PL3≈PM3). The most distal point on the lateral condyle to point Pc is noted as the medial-lateral converging point. A third asymmetric angle is defined using this relation, which we denote the Sagittal Asymmetric Angle (SAA). This angle is otherwise defined by angle <PL1-Fc-Pc or <PM1-Fc-Pc and denoted angle μ (FIG. 4B). FIG. 4C shows the relation in a 3-D femur model.

Figure 4D:
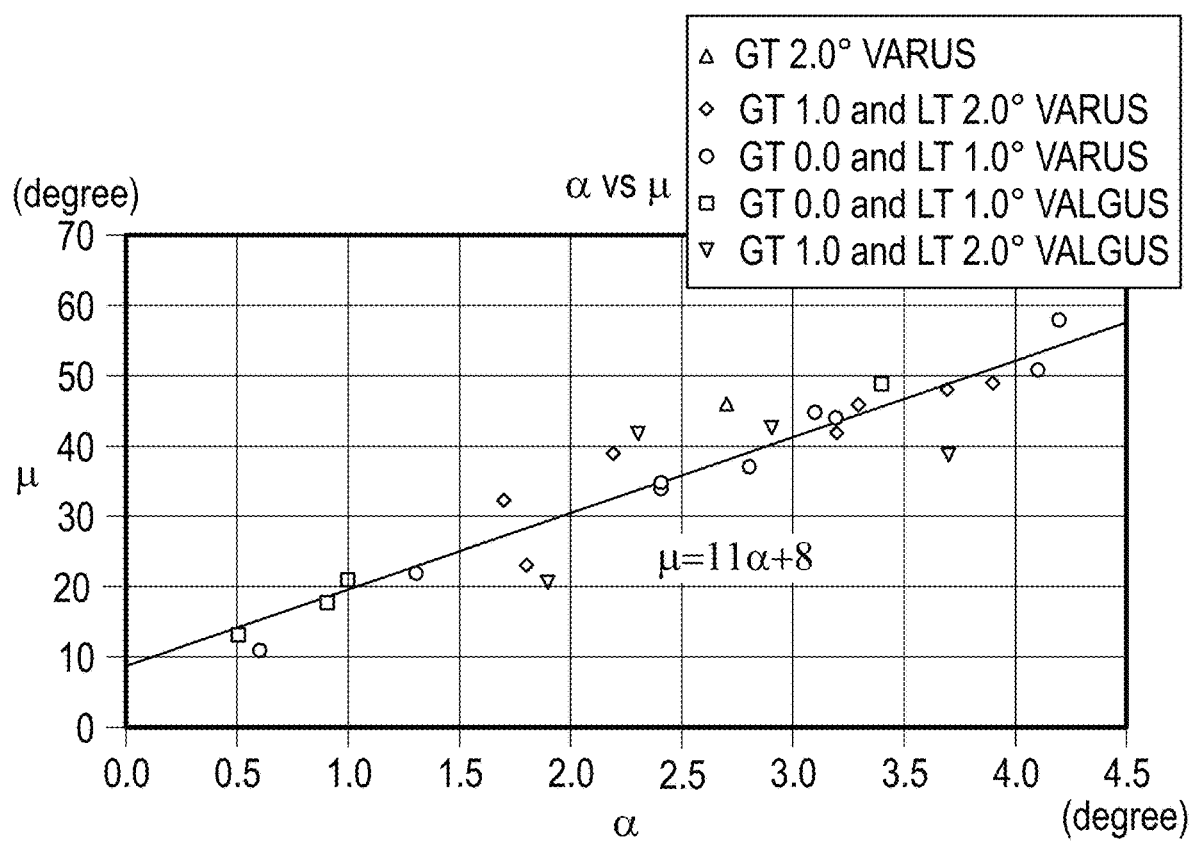
FIG. 4D is a graph of the best fit linear relation between the coronal asymmetric angle α and the sagittal asymmetric angle µ for various varus and valgus knee joints.

Just as the AAA has a functional and linear relation to the CAA, we find that the SAA (angle μ) has a functional and linear relation to the CAA (angle α) (FIG. 4D). This relation represents the amount of asymmetricity between the medial and lateral condyle for individual knees. The average μ is 36°+12°, and the angle <PL1-Fc-PL3 is approximately 120°. Notably, as angle α goes to zero, it is seen that μ approaches to 6°. It is deduced that the perfect symmetricity of the medial and lateral condyles of the knee would not exist. This latter angle likely relates to the maximal amount of deep knee flexion that can be achieved per patient. Again, the amount of asymmetricity is not found to be related to varus and valgus angle. This functional relationship demonstrates that as the CAA increases so does the amount of asymmetry along the surface of the condyles (i.e., angle μ).

Functionally, SAA (angle μ) can represent the amount of the distal femur rotation that occurs as the knee initiates flexion. A larger SAA induces an increase of the amount of distal femur rotation with a subsequent increase in the internal rotational moment. Anatomically, it is also observed that the overall size of medial and lateral epicondyles increases with larger CAA.

Theoretical Consequence of the Knee Surface Geometry Model

Figure 5A:
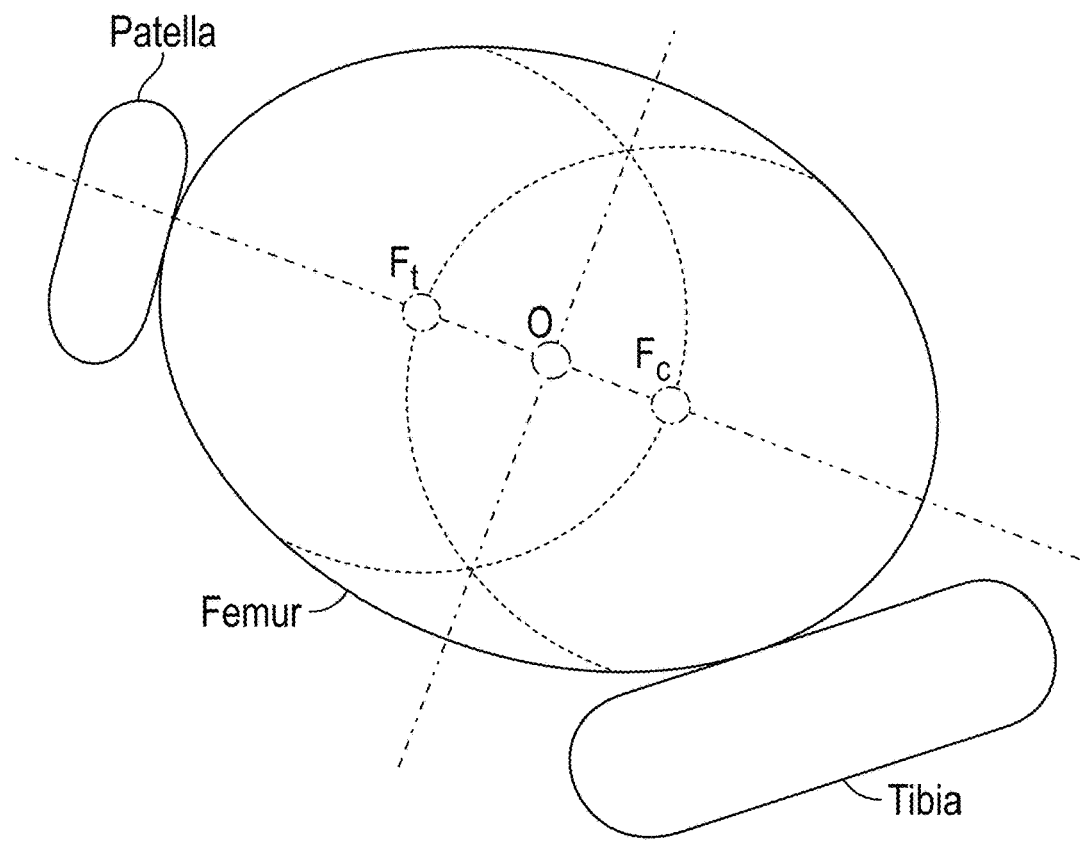
FIG. 5A is a schematic axial plane diagram illustrating the connectivity between the distal femur, proximal tibia, and patella and, in particular, as a distal femur elliptical cam model in conjunction with the patella and proximal tibia. In early flexion, the tibia is the leading follower and patella is the trailing follower. In deep flexion, the patella becomes the leading follower and tibia is the trailing follower.
Figure 5B:
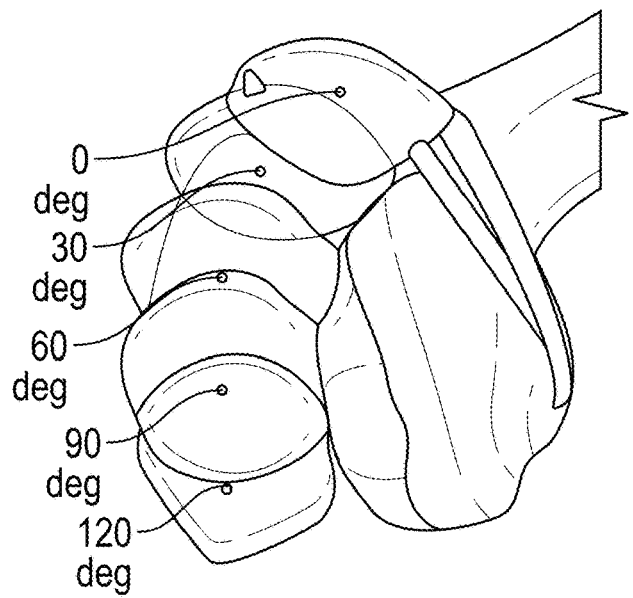
FIG. 5B is a perspective view illustrating the position of the patella at different degrees of knee flexion.
Figure 5C:
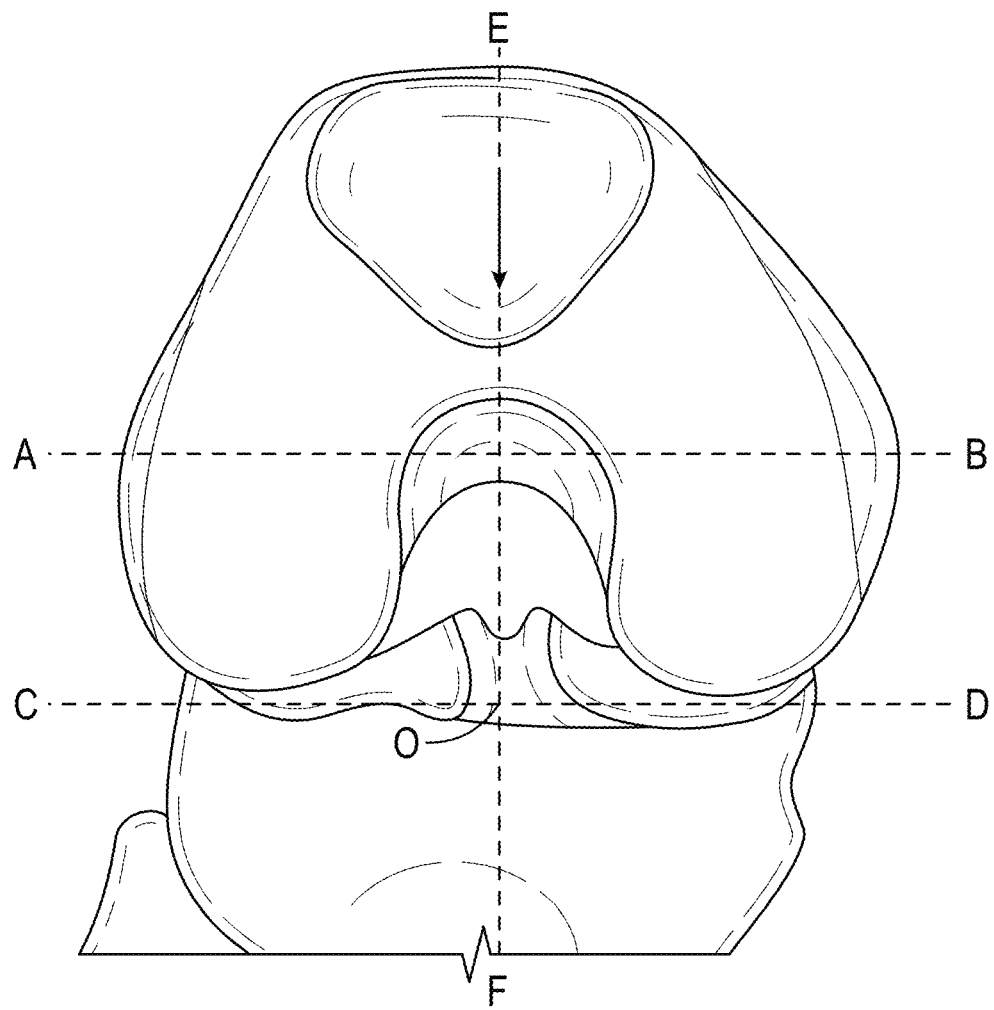
FIG. 5C is a coronal view when the knee flexion is about 30°. The patella engages with the trochlear groove and follows line EF.

As shown in FIG. 5, there is connectivity between the patella, distal femur and proximal tibia that is established during knee flexion. This connectivity is summarized by the characteristics of the proposed elliptical model with the asymmetric parameters α, β, and μ. This model approximates the distal femur as an elliptical cam that controls the contact characteristics of patella and tibial plateau (FIG. 5A). As the knee flexes, the tibia works as a leading follower, and the patella works as a trailing follower. When knee flexion starts, the tensions of the MCL and LCL are each greater than the patella tendon tension; consequently, knee rotation, in addition to flexion, are the dominant mechanism. However, with deeper knee flexion, patella tendon tension gradually and monotonically increases while MCL and LCL tensions gradually and monotonically diminish. Eventually, knee rotation ceases, and the predominant mechanism is flexion and translation. This transition point occurs at the point where the knee flexes to the Medial-Lateral Condyle Converging Point (Pc) (FIG. 4B).

From this point onwards, the patella becomes leading follower, and the tibial plateau becomes trailing follower. Consequently, a smooth transition of MCL/LCL tension to patella tendon tension takes place. As the patella tendon tension increases, the distal femur translates on the tibial plateau until the knee reaches 120° flexion. This model also indicates that the characteristics of patella motion within the trochlear groove has a nearly one-to-one relation to the medial and lateral posterior condyle motion on the tibial plateau. This is signified by the equivalent radius of curvature (R) defined by the circles modeling the medial and lateral condyles beyond point Pc and the trochlear groove (FIG. 3B). Thus, as the knee flexes past than Medial-Lateral Condyle Converging Point Pc, knee motion becomes close to cylindrical motion. This assures a smooth dynamic motion from the Medial-Lateral Condyle Converging Point to approximately 120° (or more) flexion position. However, although patellar tendon tension causes the distal femur to translate posteriorly, further translation of the lateral condyle is restricted by the anterior cruciate ligament (ACL) where it has its origin. Similarly, as the knee goes from flexion to full extension, the posterior cruciate ligament [PCL] may play an important role in restricting the reverse translation of medial condyle to induce the distal femur rotation. It can be concluded that the center point O of the elliptical model would be the absolute dynamic center of the distal femur (FIG. 5A).

From full extension to the Medial-Lateral Condyle Converging Point (Pc), knee motion involves flexion, rotation, and translation. In early flexion, the patella most likely goes through transient motion. During this period of transient motion, the patella tendon tension is not yet fully developed but the amount of tension may be tight enough for the patella to be kept within the pocket of trochlear groove. As shown in FIG. 4B, this transient motion seems to occur from 0° to the medial-lateral converging angle (the average) 36°. In other words, the patella's absolute path may not be observed; rather, many slightly irregular motions can be observed within the trochlear groove. When knee flexion passes point Pc and the patella tendon tension increases, patella motion is further restricted by the features of the trochlear groove. The irregular motion of the patella then converges to a position between the distal medial and lateral condyles in a steady state motion (i.e., patellar tracking follows the Line EF that is perpendicular to posterior condyle reference line CD and NBA as shown in FIG. 5B). Furthermore, as the knee continues to flex, patella tendon tension reaches its maximum, leading to the conclusion that the steady state motion ensures the patella tracks within the medial and lateral distal condyles and establishes the absolute stability of knee. It is important to be noted that this model also signifies that the anatomical Varus/Valgus angle of each individual not only plays an important role for the lower limb structural stability at the full extension, but also is directly linked to the patella tracking motion and stability during knee flexion.

Tibial Slope

Figure 6A:
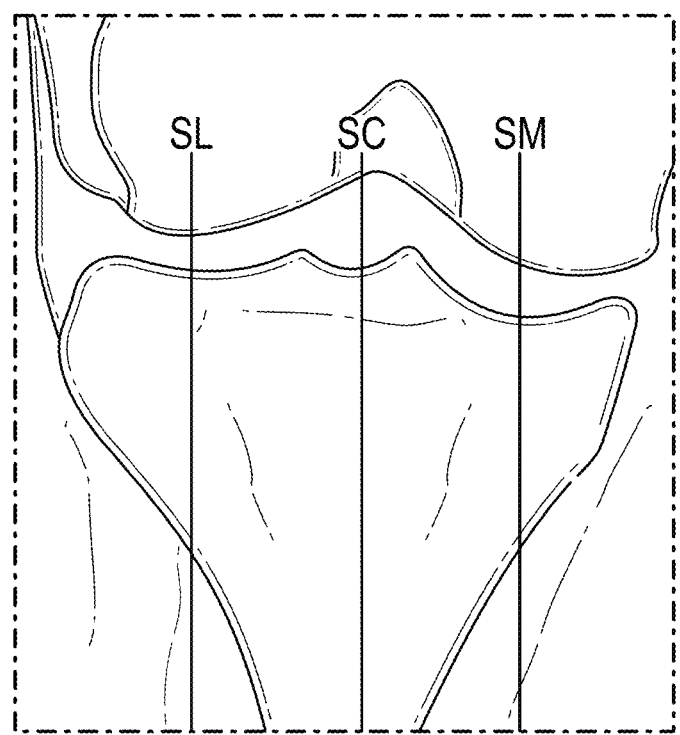
FIGS. 6A-6D are knee joint images arranged along NBA axis in coronal view (6A and 6C) and tibial mechanical axis in sagittal view (6B and 6D) for defining the tibial slope ψ and the angle difference ϕ of medial to lateral tibial slope.
Figure 6B:
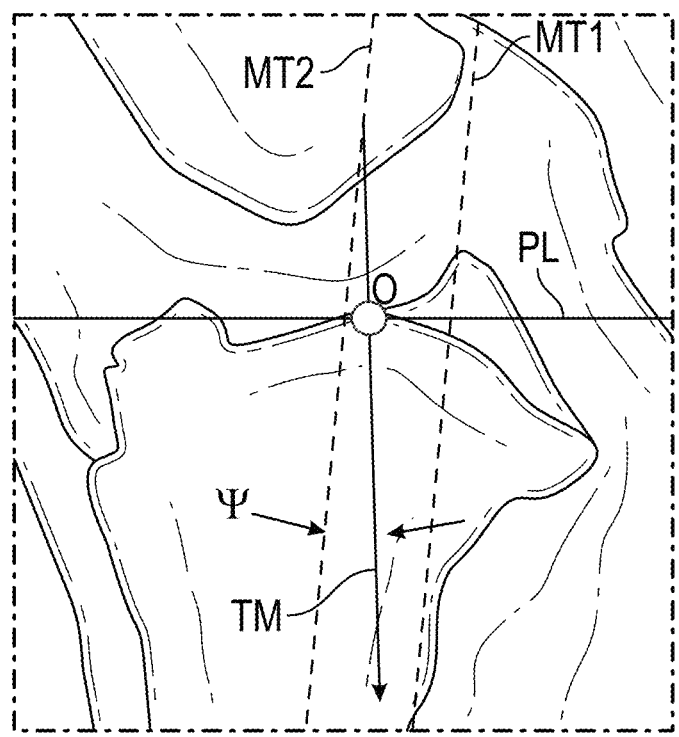
Figure 6C:
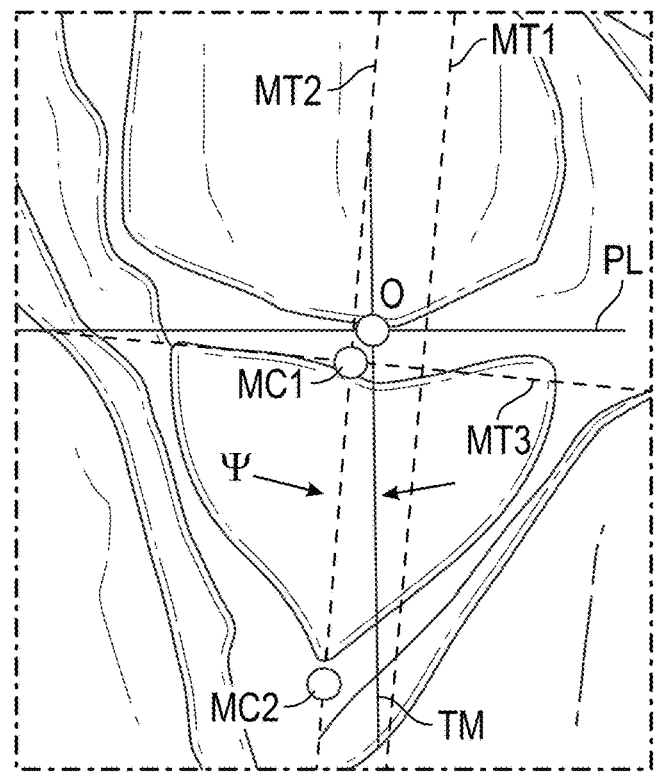
Figure 6D:
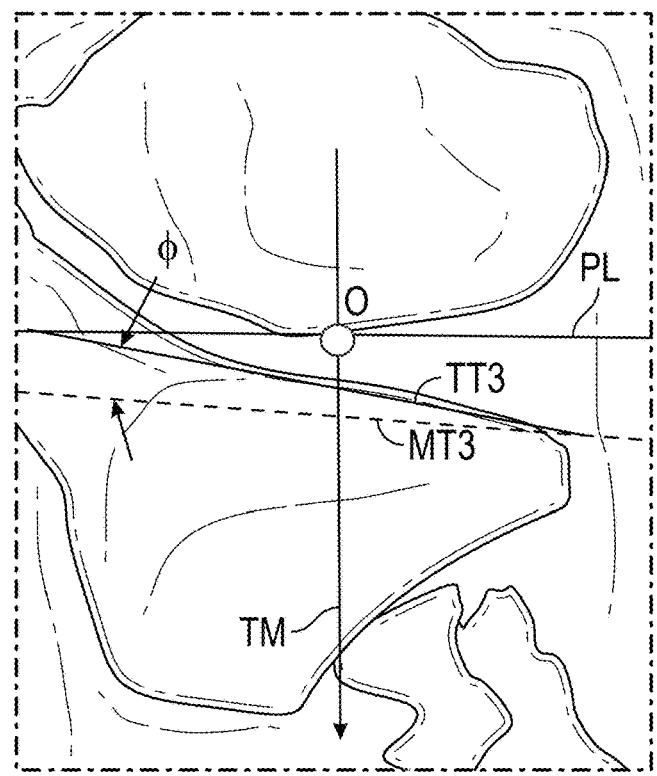

FIGS. 6A-6D are arranged along NBA axis in coronal view and tibial mechanical axis in sagittal view. In the sagittal view of a MRI medial tibia slice SM, shown in FIGS. 6A and 6C, line MT2 is defined as the line includes Point MC1, the midpoint of medial tibia plateau, and Point MC2, the endpoint of medial tibia. Further, as shown in FIG. 6B at MRI slice SC in FIGS. 6A and 6B, line MT1 is defined as the line parallel to MT2 and asymptotic to posterior tibia wall, represented by the red dots. It is important to be noted that the asymptotic line at the posterior wall provides the best angle to avoid the stress concentrations and to assure the smooth flow of stress without any interruption exerted by body weight. If these two conditions are met, the medial tibial slope MT0. Perpendicular to both MT1 and MT2, is estimated and represented by Angle $\psi$, shown in FIGS. 6B and 6C. The lateral tibial slope TT0 is defined at the MRI slice SL shown in FIGS. 6A and 6D. The angle $\phi$ is the angle difference of medial to lateral tibial slope. The average medial tibial slope is 3.3° with the standard deviation of 1.1°. However, it is observed that any functional relation of V/V angle vs $\psi$, and $\alpha$ (CAA) vs $\psi$ are not found.

Figure 6E:
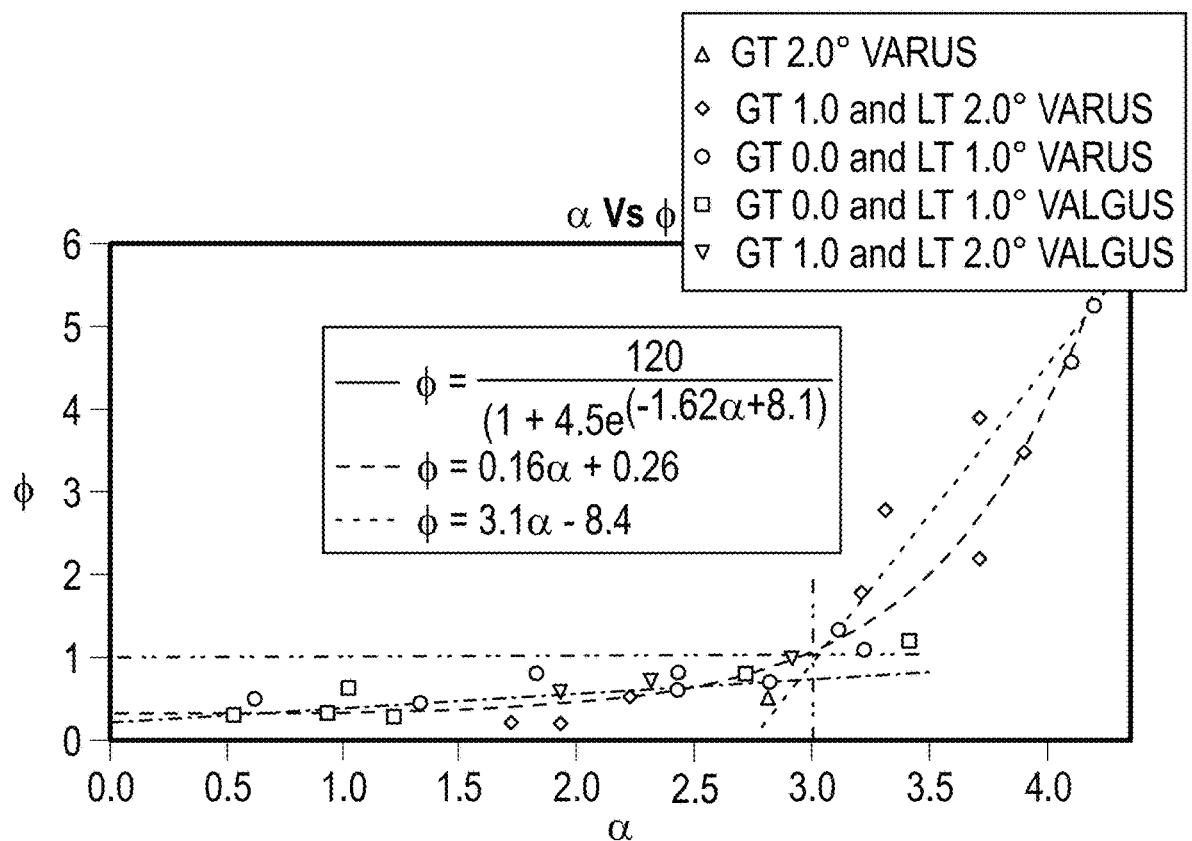
FIG. 6E is a graph of the relationship between the coronal asymmetric angle α and the medial-to-lateral tibial slope difference ϕ.

FIG. 6E illustrates the relationship between $\alpha$ and $\phi$. The two linear regression graphs are obtained with $\alpha=3°$ as a breakeven point. If $\alpha$ is less than 3°, $\phi$ is less than 1° and does not show any significant trend or gradual increase up to $\phi=1'$. It can be deduced that in this range, medial tibial slope is nearly same as lateral tibial slope within 1°. It should be noted that another constraint regarding medial and lateral slopes is their slopes cannot have inverted directions each other. However, if $\alpha$ is greater than 3°, the drastic change in lateral tibial slope can be observed.

Furthermore, as shown in FIG. 6E, a sigmoid activation function is utilized in the range of $0<\alpha<4.5$ and includes the point of $\alpha=3$ and $\phi=1$ to propose the continuous transition of $\alpha$ and $\phi$. From a structure point of a view, FIG. 6E provides valuable information regarding the structural stability of the lower limb alignment. However, FIG. 6E does not fully demonstrate the geometrical features of asymmetrical distal condyles, $\alpha$. Consequently, the cartilage formation of both medial and lateral tibial plateaus in sagittal view needs to be analyzed.

Figure 7A:
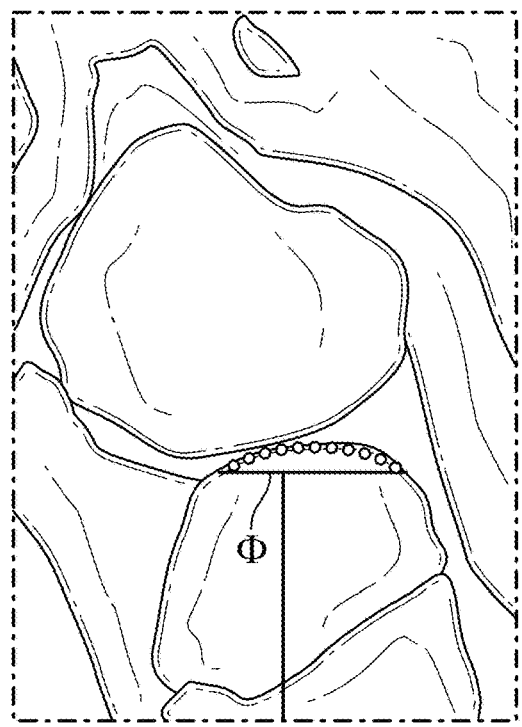
FIGS. 7A-7I exhibit sagittal views of medial and lateral tibial plateau where they make the contacts with distal medial and lateral condyles. In order to comprehend the parameter ϕ, each MRI image is rotated in order that medial tibial slope is shown to be zero degree. Three cases are considered.
Figure 7B:
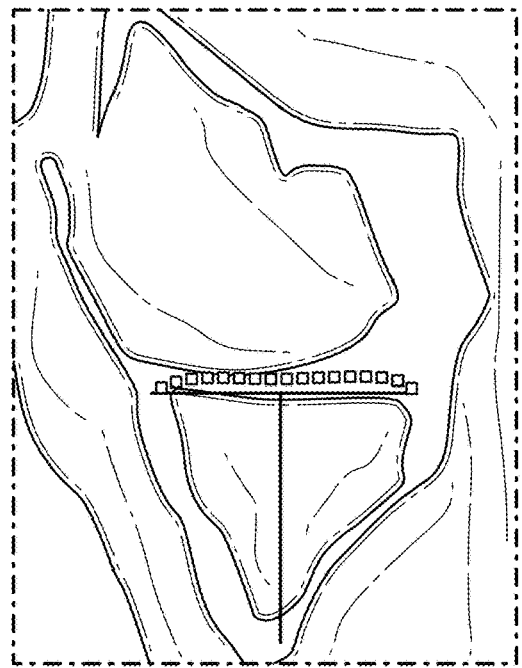
Figure 7C:
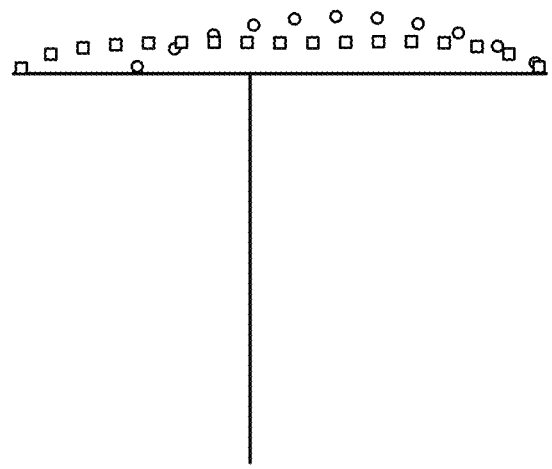
Figure 7D:
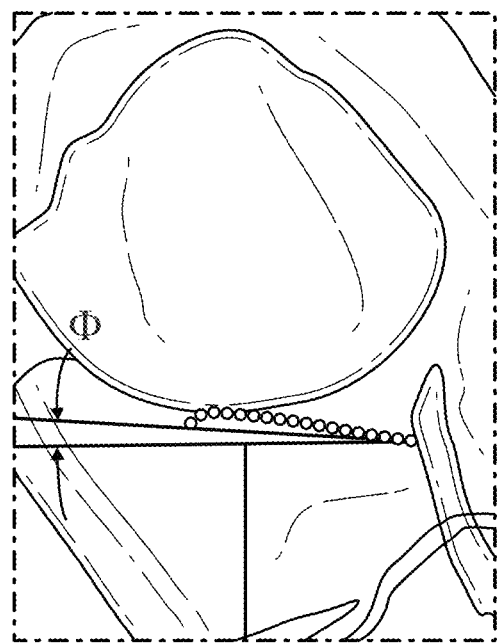
Figure 7E:
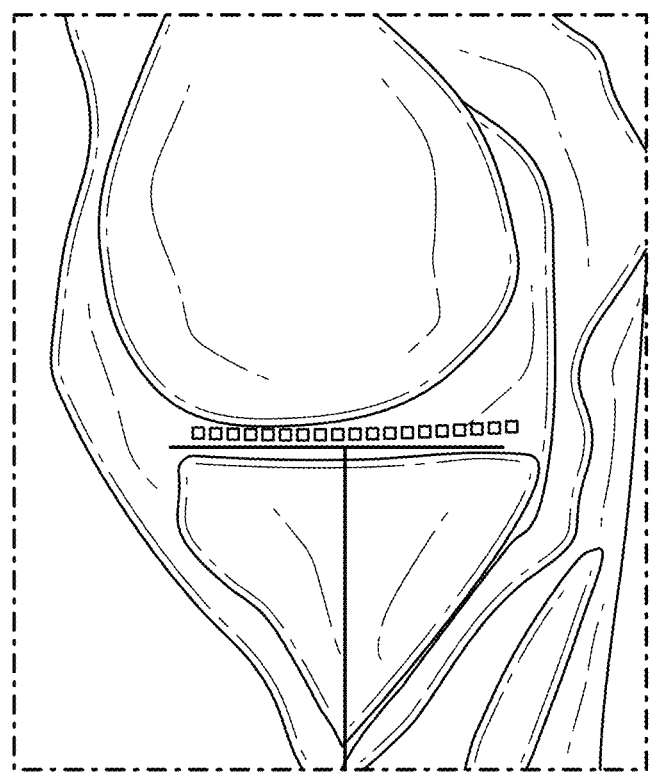
Figure 7F:
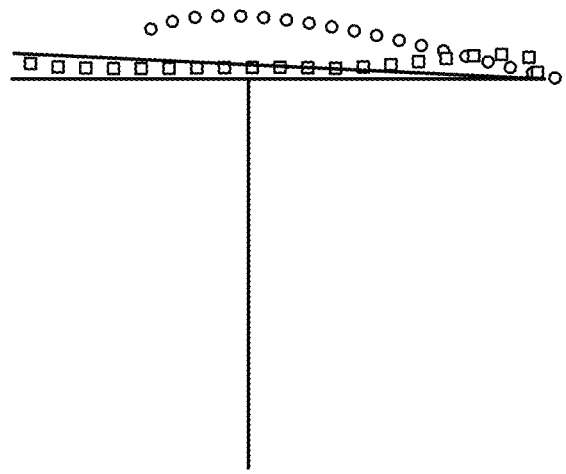
Figure 7G:
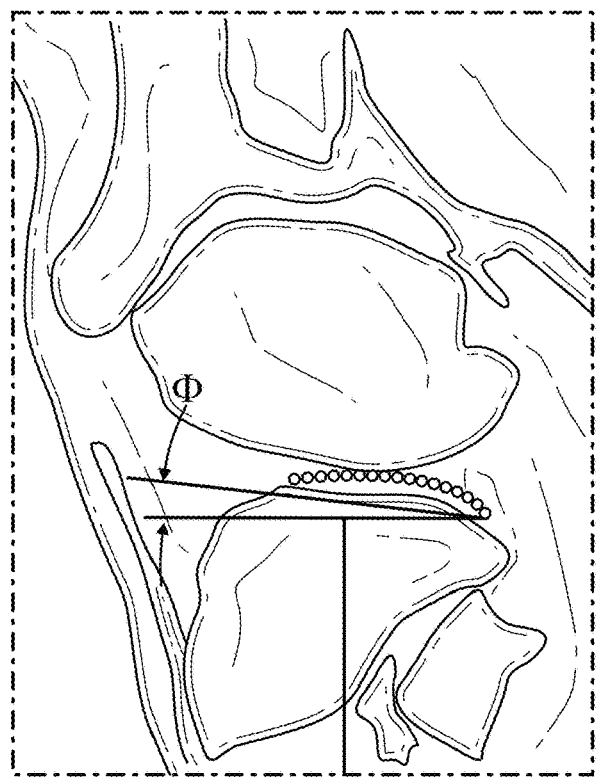
Figure 7H:
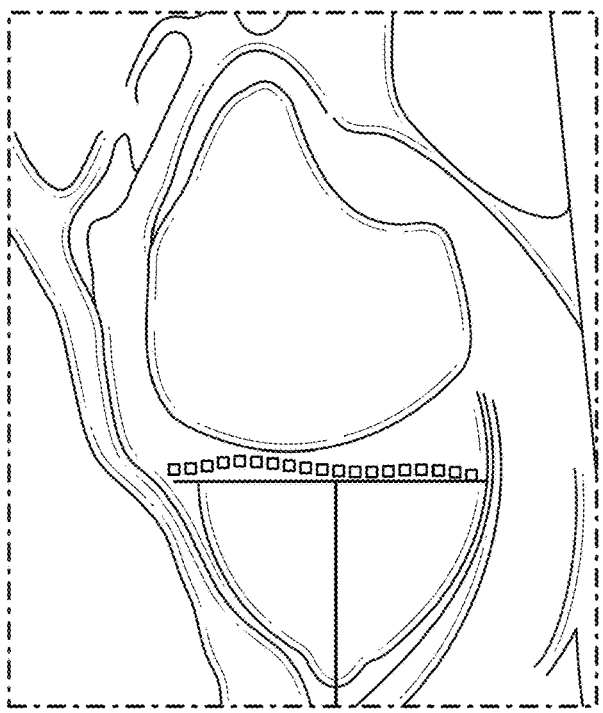
Figure 7I:
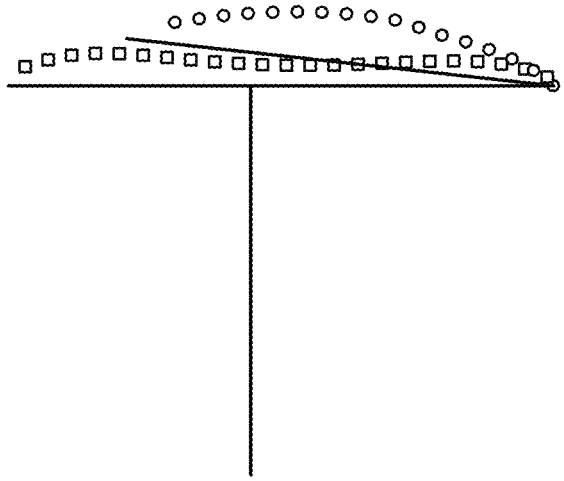

FIGS. 7A-7I exhibit sagittal views of the medial and lateral tibial plateau where they make the contacts with distal medial and lateral condyles. In order to comprehend the parameter $\phi$, each MRI image is rotated in order that medial tibial slope is shown to be zero degree. In FIGS. 7A-7C, wherein V/V angle is 0.1° valgus, $\alpha=0.5°$, and $\phi=0.3°$, the medial side of cartilage shows the near flat surface while the medial side of cartilage shows the circular shape. However, the superimposition of the two surface profiles indicates that they are close enough to be considered near symmetric and approximately share the same tibial slopes. In FIGS. 7D-7F, wherein V/V angle is 1.7° valgus, $\alpha=3.7°$, and) $\phi=3.9°$ and in FIGS. 7G-7I, wherein V/V angle is 2.1° varus, $\alpha=4.2°$, and $\phi=5.3°$, although the drastic change in lateral tibial slope compared to medial tibial slope is observed, the superimposition of medial and lateral surface profiles shows significant asymmetric characteristics. The medial cartilage surface profiles are still near flat shape while the lateral cartilage surface profiles are subtle or peculiar difference. However, it is important to be observed in all three cases that both cartilage surface profiles have tendency to converge each other at the posterior of the tibia. It can be deduced that as the knee flexes close to 90° along with translation motion, the contact points between and femoral condyles and tibial plateaus approach toward the posterior side of tibial plateau. As a result, the knee flexion undergoes close to cylindrical motion that assures the knee flexion of 120°.

Also, another interesting observation is that from CAM mechanics point of view, the dynamic contact characteristic on the medial side is near linear motion due to flat nature of medial cartilage surface profile along with the circular condyle shape. Whereas the dynamic contact characteristic on the lateral side is near cycloidal motion due to circular nature of lateral cartilage surface profile along with the circular condyle shape. Cycloidal motion has the best dynamic characteristics in terms of controlling acceleration and yielding a mechanism with the low vibration, stress, and shock characteristics. The knee flex is a very intriguing mechanism that the linear motion on the medial side and cycloidal motions on the lateral side are executed in harmony. Although the precise mechanism is unknown, it can be deduced that this mechanism would induce knee rotation to achieve the knee flexion more than 120°. In case of FIGS. 7A-7C, the high knee flexion could be achieved with small knee rotation due to near symmetric nature of tibial plateau. However, in the two cases of FIGS. 7D-7F and 7G-7I, the high knee flexion would require substantial knee rotation due to asymmetric nature tibial plateau. The cycloidal motion of the peculiar lateral cartilage surface profile would assist the high knee rotation in knee flex motion in concert with the force exerted by patella tendon.

As shown in FIG. 7, it is also interesting to be observed that the contact point of the lateral condyle and tibial plateau is around the tip of the circular shape of the lateral cartilage surface where the tibial slope is close to zero. Based on the definition of cycloidal motion, it can be seen that the initial conditions of knee flexion at the full extension are zero velocity and the maximum finite value of acceleration. Furthermore, this is the best location for PCL to constrain lateral condyle motion. At last, it is noted that continuous curve of Sigmoid activation function in FIG. 6E would be considered as the lower bound to determine the lateral tibial slope with respect to a.

Figure 8A:
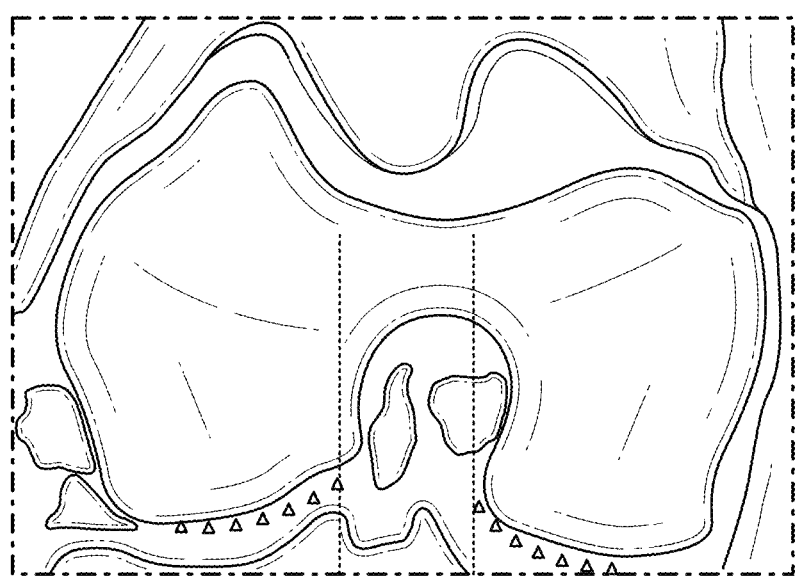
FIGS. 8A-8E exhibit the cartilage surface profiles of distal condyles of femur in coronal view (8A), tibial plateau near the spine peaks (8B) and mid-patella (8C).
Figure 8B:
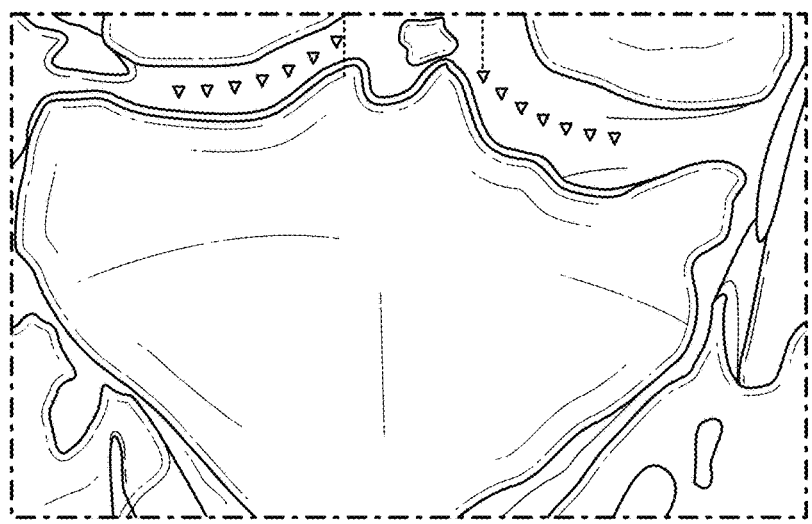
Figure 8C:
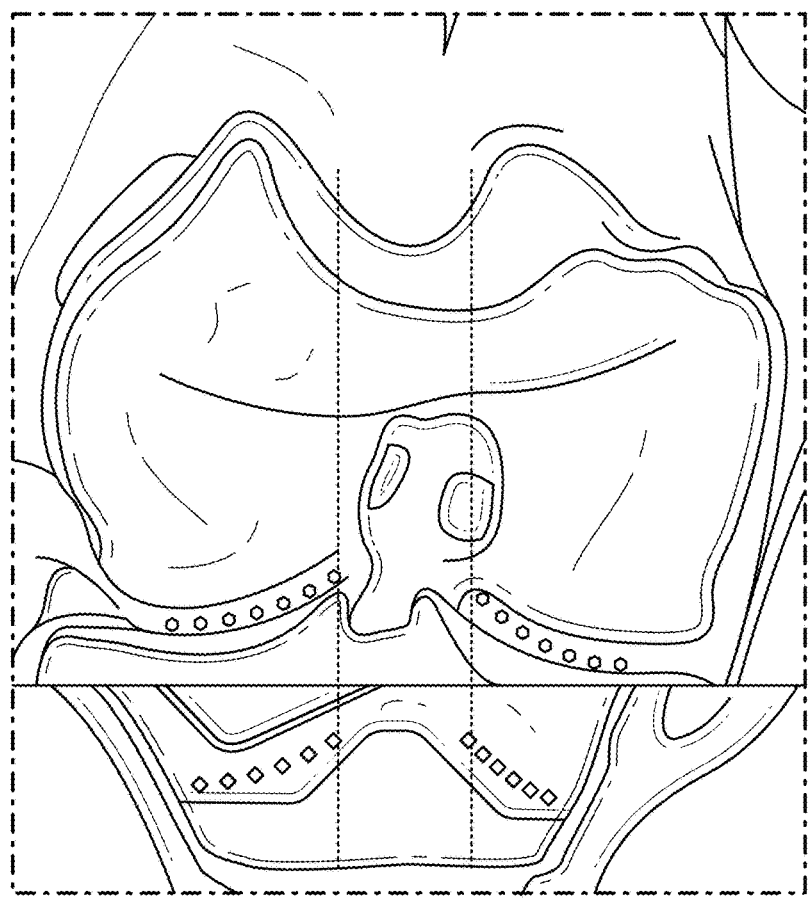

FIGS. 8A-8C exhibit the cartilage surface profiles of distal condyles of femur in coronal view (8A), tibial plateau near the spine peaks (8B) and mid-patella (8C). FIGS. 8A and 8B show that the two surface profiles are almost identical. It is obvious that at the full extension of knee (0° flexion), the two surfaces should match each other for the perfect contact conditions between distal femur and proximal tibia. It can be also observed that around 160° flexion, the patella slides down to around distal condyles and makes a contact on the surface of distal condyles.

Figure 8D:
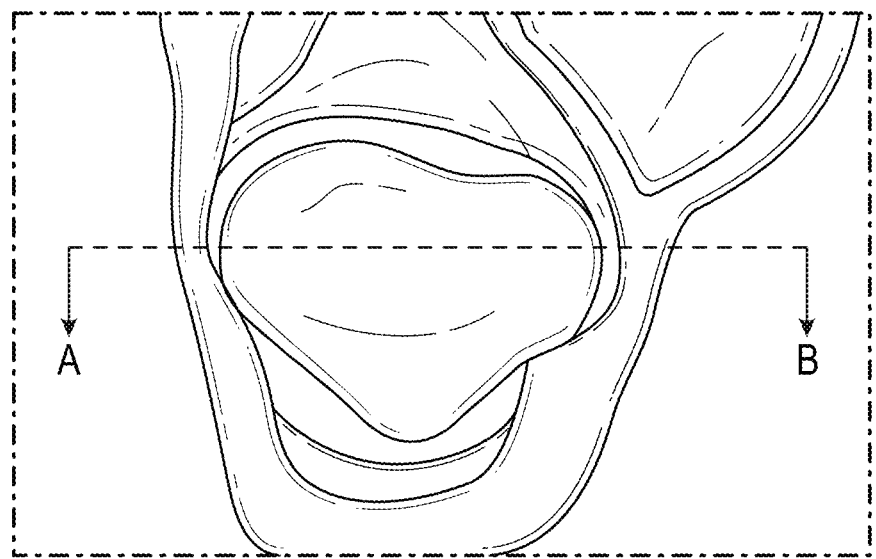
Figure 8E:
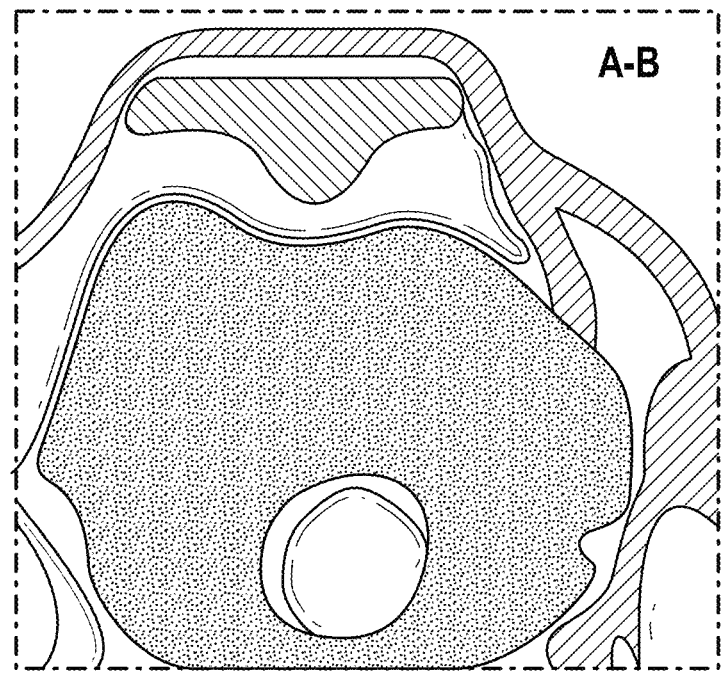
Figure 9A:
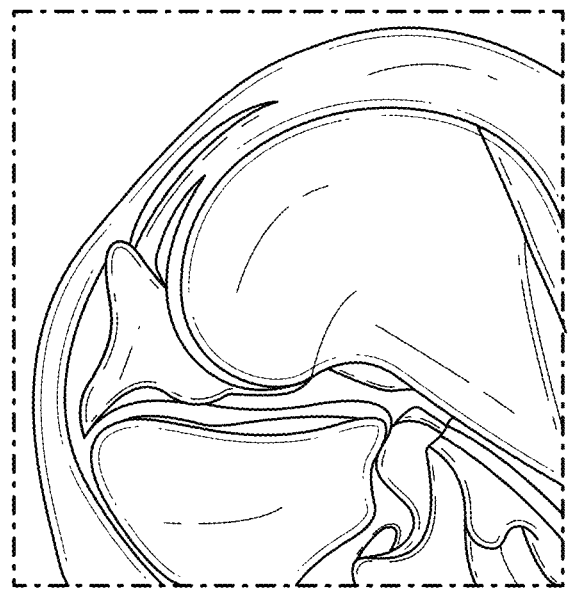
FIGS. 9A-9B are MRI images of medial and lateral knee position at 163° flexion.
Figure 9B:
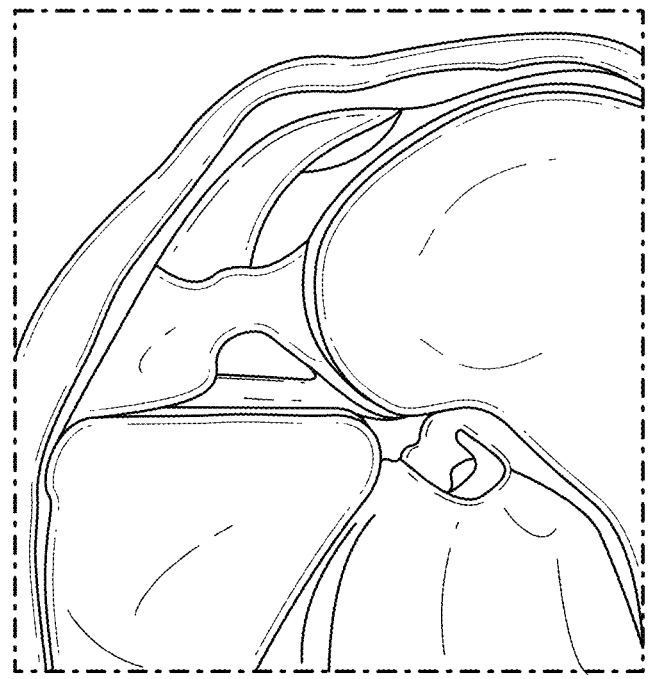
Figure 9C:
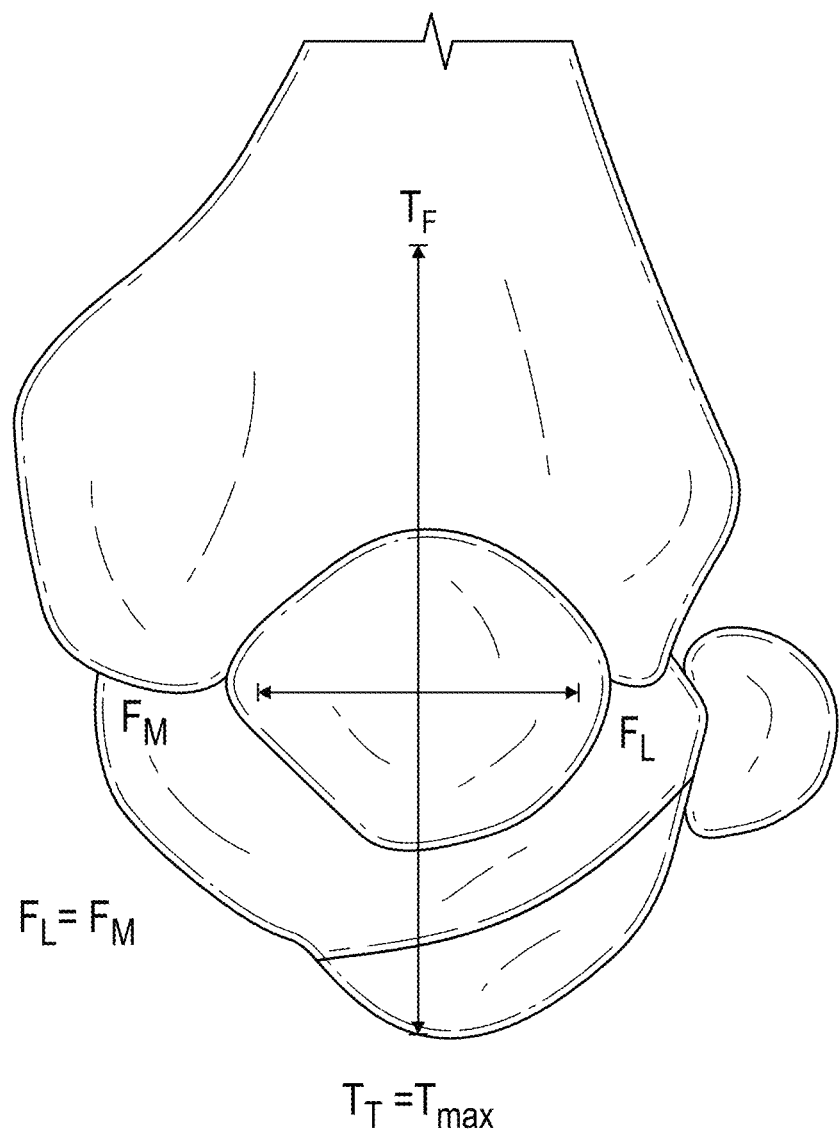
FIG. 9C is a schematic coronal plane diagram illustrating tibial and femoral patella tension forces in FIGS. 9A-9B.

FIGS. 9A and 9B are obtained and exhibit the MRI images of medial and lateral knee position at 163° flexion. They clearly show the external rotation of the knee that the lateral condyle of the distal femur makes a contact at the posterior of the lateral tibial plateau, whereas the medial condyle of femur makes a contact around mid-point of medial tibial plateau. At full flexion, it is observed that the patella is positioned near the distal condyles of femur, and the patella tendon would be under the maximum tension. Therefore, to stabilize patella onto distal the condyles, the identical surface profiles between the distal condyles of femur and patella should make a geometrically near perfect match each other. FIGS. 8D and 8E show that the surface profile of A-B cross section is very close to that of distal condyles of femur. Also, from the mechanical stability of a view, another important requirement is that the patella tension direction should be straight, and TF and TT have the same magnitude of Tmax with opposite direction in FIG. 9C. Consequently, the forces of FM and FL should be near zero, which prevents the patella from dislocation from the distal condyles of femur. The external rotation of 120° to full flexion would not have a functional relation to CAA ($\alpha$). However, it should be pointed that the external rotation of 120° to full flexion is required for the patella stability at the full flexion of knee. Furthermore, FIGS. 8A-8C and 9A-9B show the connectivity between patella and tibia.

The invention claimed is:

1. A computer-aided method using an interactive preoperative planning software analysis tool for establishing, from patient-specific images, implant parameters and customizing selection of a total knee replacement prosthesis to a patient, the method comprising:
    obtaining, and inputting as image data into a computer system, a series of images of a leg of a patient, including at least a set of coronal, axial and sagittal image slices of a knee joint representing a current anatomical condition of a patient;
    determining by the computer system a neutral boundary axis, a set of epicondylar and trochlear features that define an elliptical cam, and a medial-lateral tibial slope, from the image data;
    defining, by the computer system from the determined epicondylar features, a sagittal plane containing a most posterior point of a medial condyle and identifying in that sagittal plane a most distal point P1 of the medial condyle, the most posterior point P2 of the medial condyle, and an end point P3 of the medial condyle at deepest flexion, the three points P1, P2 and P3 defining a first circle with a center point Fc and a radius R;
    defining, by the computer system from the determined trochlear features, a sagittal plane containing a deepest aspect of a trochlear groove and identifying in that sagittal plane a distal trochlear groove point Q1, a mid-trochlear groove point, and an anterior trochlear groove point Q3, the three points Q1, Q2 and Q3 defining a second circle with a center Ft with a radius R, the first and second circles overlapping;
    defining an ellipse with eccentricity 0.25 and focal points Fc and Ft; and
    constructing knee prosthesis components with dimensions determined from the image data, the knee prosthesis having a femoral component as an elliptical cam with dimensions defined by the ellipse, and having tibial and patellar components interacting with the femoral component as cam followers under knee flexion.

2. The method as in claim 1, further comprising estimating by the computer system from the determined set of features a coronal asymmetry angle $\alpha$; and selecting a prosthesis, from among a set of prosthesis with differing coronal asymmetry angle, based on the estimated coronal asymmetry angle, a symmetric prosthesis being selectable whenever $\alpha \leq 2.5°$ and an asymmetric prosthesis with closely matching a being selectable whenever $\alpha > 2.5$.

3. The method as in claim 1, further comprising defining, by the computer system from the determined epicondylar features, a sagittal asymmetric angle $\mu$ representing a lateral femoral condyle asymmetric surface profile defined by a medial-lateral condyle converging point PC, the focal point Fc, and a distal point of the lateral condyle, and constructing the knee prosthesis femoral component with a corresponding sagittal asymmetric angle.

4. The method as in claim 1, wherein the femoral component has a larger medial condyle than lateral condyle to force axial rotation under knee flexion, the relative degree of medial-to-lateral condyle difference being defined by a medial-lateral tibial slope difference from the image data.

5. The method as in claim 1, further comprising defining, by the computer system from coronal and sagittal slices in the image data through midpoints of medial and lateral tibia plateaus, medial and lateral tibial slopes MT0 and TT0 and an angle difference $\phi$ between them, and constructing the knee prosthesis tibial component with a corresponding medial-lateral tibial slope angle difference.

6. A computer-aided method using an interactive preoperative planning software analysis tool for establishing, from patient-specific images, implant parameters and customizing selection of a total knee replacement prosthesis to a patient, the method comprising:

obtaining, and inputting as image data into a computer system, a series of images of a leg of a patient, including at least a set of coronal, axial and sagittal image slices of a knee joint representing a current anatomical condition of a patient;

determining by the computer system a neutral boundary axis, a set of epicondylar and trochlear features that define an elliptical cam, and a medial-lateral tibial slope, from the image data;

estimating by the computer system from the determined set of features a coronal asymmetry angle $\alpha$;

selecting a prosthesis, based on the estimated coronal asymmetry angle, from among a set of prosthesis with differing coronal asymmetry angle, a symmetric prosthesis being selectable whenever $\alpha \leq 2.5°$ and an asymmetric prosthesis with closest $\alpha$ being selectable whenever $\alpha > 2.5°$; and constructing the knee prosthesis components with dimensions determined from the image data.

7. The method as in claim 6, further comprising defining, by the computer system from the determined epicondylar features, a sagittal asymmetric angle $\mu$ representing a lateral femoral condyle asymmetric surface profile defined by a medial-lateral condyle converging point PC, the focal point Fc, and a distal point of the lateral condyle, and constructing the knee prosthesis femoral component with a corresponding sagittal asymmetric angle.

8. The method as in claim 6, wherein the femoral component has a larger medial condyle than lateral condyle to force axial rotation under knee flexion, the relative degree of medial-to-lateral condyle difference being defined by a medial-lateral tibial slope difference from the image data.

9. The method as in claim 6, further comprising defining, by the computer system from coronal and sagittal slices in the image data through midpoints of medial and lateral tibia plateaus, medial and lateral tibial slopes MT0 and TT0 and an angle difference $\phi$ between them, and constructing the knee prosthesis tibial component with a corresponding medial-lateral tibial slope angle difference.

* * * * *